(12) United States Patent
Bratkovski et al.

(10) Patent No.: US 7,528,948 B2
(45) Date of Patent: May 5, 2009

(54) CONTROLLABLE SURFACE ENHANCED RAMAN SPECTROSCOPY

(75) Inventors: Alexandre Bratkovski, Palo Alto, CA (US); Duncan R. Stewart, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 345 days.

(21) Appl. No.: 11/493,477

(22) Filed: Jul. 25, 2006

(65) Prior Publication Data

US 2008/0024776 A1 Jan. 31, 2008

(51) Int. Cl.
*G01J 3/44* (2006.01)
*G01N 21/65* (2006.01)

(52) U.S. Cl. ...................................... 356/301
(58) Field of Classification Search ................... 356/301
See application file for complete search history.

(56) References Cited

U.S. PATENT DOCUMENTS

| | | | |
|---|---|---|---|
| 4,674,878 A | 6/1987 | Vo-Dinh | |
| 7,016,034 B2 | 3/2006 | Holz et al. | |
| 7,245,370 B2 * | 7/2007 | Bratkovski et al. | 356/301 |
| 7,307,719 B2 * | 12/2007 | Wang et al. | 356/301 |
| 7,342,656 B2 * | 3/2008 | Islam et al. | 356/301 |
| 2005/0083533 A1 | 4/2005 | Atia et al. | |
| 2005/0206892 A1 | 9/2005 | Wang et al. | |
| 2006/0055920 A1 | 3/2006 | Wang et al. | |
| 2006/0146323 A1 | 7/2006 | Bratkovski et al. | |
| 2006/0147148 A1 | 7/2006 | Wang et al. | |
| 2007/0086001 A1 | 4/2007 | Islam et al. | |

OTHER PUBLICATIONS

Penn State Applied Research Laboratory, "Electro-Optics—Current Projects", http://www.arl.psu.edu/capabilities/mm_mfgsys_electro.html (downloaded Jul. 20, 2006).
Wei, A., et. al., "Resorcinarene-Encapsulated Nanoparticles: Building Blocks for Self-Assembled Nanostructure," J. Inclusion Phenom. and Macrocyclic Chem. 41: 83-86 (2001).
Lu, Y., et. al., "High-Density Silver Nanoparticle Film with Temperature-Controllable Interparticle Spacing for a Tunable surface . . . ", Nano Letters, vol. 5, No. 1, 5-9 (2005).
Hung, P., et. al., "Microfabricated Suspensions for Electrical Connections on the Tunable Elastomer Membrane," App. Phys. Lett., vol. 85, No. 24, 6051-3 (Dec. 13, 2004).
Kamins, T et al—"Growth and Structure of Chemically Vapor Deposited Ge Nanowires on Si Substrates"—nano Letters vol. 4, No. 3—Jan. 23, 2004—pp. 503-506.

* cited by examiner

*Primary Examiner*—L. G Lauchman (57) ABSTRACT

An apparatus and related methods for facilitating surface-enhanced Raman spectroscopy (SERS) is described. The apparatus comprises a SERS-active structure near which a plurality of analyte molecules are disposed and an actuation device in actuable communication with the SERS-active structure to deform the SERS-active structure while the analyte molecules are disposed therenear. The deformation of the SERS-active structure varies an intensity of radiation Raman-scattered from the analyte molecules.

20 Claims, 5 Drawing Sheets

CONTROLLABLE SURFACE ENHANCED RAMAN SPECTROSCOPY

FIELD

This patent specification relates to Raman spectroscopy. More particularly, this patent specification relates to Surface Enhanced Raman Spectroscopy (SERS) in which SERS-active structures are used to intensify Raman signals from analyte molecules disposed adjacent thereto or adsorbed thereonto.

BACKGROUND

Raman spectroscopy is a technique for performing chemical analysis. High intensity monochromatic light, such as that provided by a laser, is directed onto an analyte molecule (or sample) that is to be chemically analyzed. A majority of the incident photons are elastically scattered by the analyte molecule, wherein the scattered photons have the same energy (and, therefore, the same frequency) as the incident photons. This elastic scattering is termed Rayleigh scattering, and the elastically scattered photons and radiation are termed Rayleigh photons and Rayleigh radiation, respectively. However, a small fraction of the photons (e.g., about 1 in $10^7$ photons) are inelastically scattered by the analyte molecules. These inelastically scattered photons have a different frequency than the incident photons. This inelastic scattering of photons is termed the Raman effect. The inelastically scattered photons may have frequencies greater than, or, more typically, less than the frequency of the incident photons.

When an incident photon collides with a molecule, energy may be transferred from the photon to the molecule or from the molecule to the photon. When energy is transferred from the photon to the molecule, the scattered photon will emerge from the sample having a lower energy and a corresponding lower frequency. These lower-energy Raman scattered photons are commonly referred to in Raman spectroscopy as the Stokes radiation. A small fraction of the analyte molecules are already in an energetically excited state. When an incident photon collides with an excited molecule, energy may be transferred from the molecule to the photon, which will emerge from the sample having a higher energy and a corresponding higher frequency. These higher-energy Raman scattered photons are commonly referred to in Raman spectroscopy as the anti-Stokes radiation.

The Stokes and the anti-Stokes radiation is detected by a detector, such as a photomultiplier or a wavelength-dispersive spectrometer, which converts the energy of the impinging photons into an electrical signal. The characteristics of the electrical signal are at least partially a function of the energy (or wavelength, frequency, wave number, etc.) of the impinging photons and the number of the impinging photons per unit time (intensity). The electrical signal generated by the detector can be used to produce a spectral graph of intensity as a function of frequency for the detected Raman signal (i.e., the Stokes and anti-Stokes radiation). A unique Raman spectrum corresponding to the particular analyte may be obtained by plotting the intensity of the inelastically scattered Raman photons against their frequency or, equivalently and more commonly, their wavenumber in units of inverse centimeters. This unique Raman spectrum may be used for many purposes such as identifying an analyte, identifying chemical states or bonding of atoms and molecules in the analyte, and determining physical and chemical properties of the analyte. Raman spectroscopy may be used to analyze a single molecular species or mixtures of different molecular species. Furthermore, Raman spectroscopy may be performed on a number of different types of molecular configurations, such as organic and inorganic molecules in either crystalline or amorphous states.

Molecular Raman scattering of photons is a weak process. As a result, powerful, costly laser sources typically are used to generate high intensity excitation radiation to increase the weak Raman signal for detection. Surface enhanced Raman spectroscopy (SERS) is a technique that allows for generation of a stronger Raman signal from an analyte relative to non-SERS Raman spectroscopy for a sample with the same number of analyte molecules. In SERS, the analyte molecules are adsorbed onto, or placed adjacent to, an activated metal surface or structure, termed herein a SERS-active structure. The interactions between the molecules and the surface cause an increase in the strength of the Raman signal. Several SERS-active structures have been employed in SERS techniques, including activated electrodes in electrolytic cells, activated metal colloid solutions, and activated metal substrates such as a roughened metal surface or metal islands formed on a substrate. For example, it has been shown that adsorbing analyte molecules onto or near a specially roughened metal surface made from silver or gold may enhance the Raman scattering intensity by factors of between $10^3$ and $10^6$.

As used herein, SERS-active material refers to the metallic material (or other material that can be found to have a similar effect) that is distributed across the substrate to form the SERS-active structures. As used herein in the context of SERS-active material, nanosection refers to any particular localized section of SERS-active material, such as an island of SERS-active material, a colloidal particle of SERS-active material, or other localized segment such as may be associated with a particular surface bump or portion of a differently shaped surface. Thus, any particular SERS-active structure comprises a patterned arrangement (which can be random, pseudorandom, or ordered) of nanosections of SERS-active material (which can be uniformly shaped or highly non-uniform and irregular in shape).

Although theories such as electromagnetic enhancement and chemical enhancement are set forth in the literature, the mechanism of Raman signal enhancement exhibited in SERS is not completely understood. Empirically, it has been observed that the intensification of the Raman scattered photons for any particular wavelength is only provided for analyte molecules in the vicinity of certain localized structures, bumps, or cavities formed by the SERS-active material (i.e., in the vicinity of certain particular patterns/shapes of SERS-active material nanosections) with sizes varying between 1 nm and several hundreds of nanometers, known as hot spots. The existence of a particular hot spot can be volatile to even small changes in any of a variety of conditions, including the local patterns/shapes of SERS-active nanosections, the position of the analyte molecule(s) relative to that location, the type of analyte molecule(s), the type of SERS-active material, and the wavelength of the incident light. In view of this volatility, it would be desirable to provide a SERS system in which increased Raman intensification can be achieved for a greater variety of analyte molecules and for greater variations in incident wavelengths, system materials, and other field conditions associated with the molecular sensing process. Other issues arise as would be apparent to one skilled in the art upon reading the present disclosure.

SUMMARY

In one embodiment, an apparatus for facilitating surface-enhanced Raman spectroscopy (SERS) is provided, comprising a SERS-active structure near which a plurality of analyte molecules are disposed and an actuation device in actuable communication with the SERS-active structure to deform the SERS-active structure while the analyte molecules are disposed therenear. The deformation of the SERS-active structure varies an intensity of radiation Raman-scattered from the analyte molecules.

Also provided is a method for facilitating surface-enhanced Raman spectroscopy in which a plurality of analyte molecules are received for attachment near a SERS-active structure. The method further comprises deforming the SERS-active structure in a vicinity of the received analyte molecules to vary an intensity of radiation Raman-scattered therefrom.

Also provided is an apparatus for use in surface-enhanced Raman spectroscopy, comprising means for deforming a SERS-active structure upon which a plurality of analyte molecules are disposed to vary an intensity of radiation Raman-scattered from the analyte molecules.

DETAILED DESCRIPTION

Figure 1:
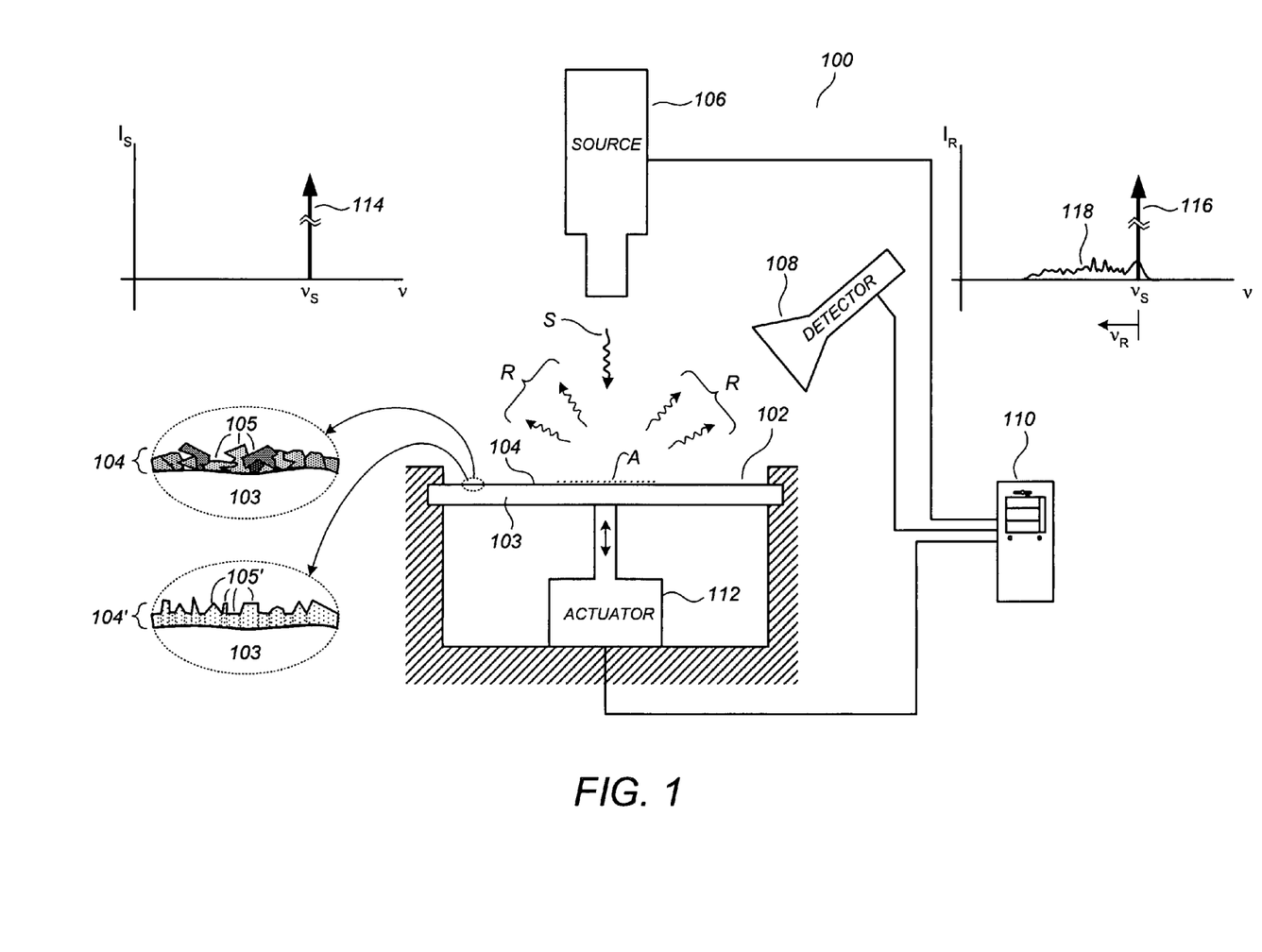
FIG. 1 illustrates a surface-enhanced Raman spectroscopy (SERS) system including an apparatus for facilitating SERS according to an embodiment.
Figure 2A:
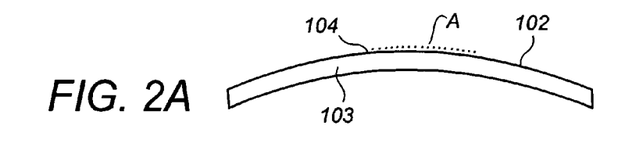
FIGS. 2A-2E illustrate a SERS-active structure at different amounts of deformation according to an embodiment.
Figure 2B:
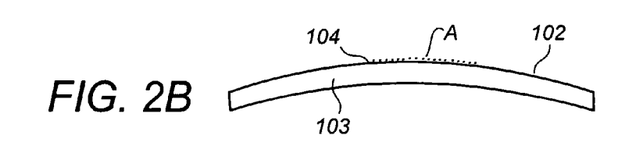
Figure 2C:
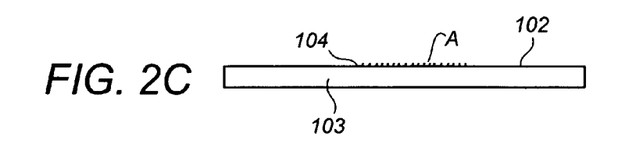
Figure 2D:
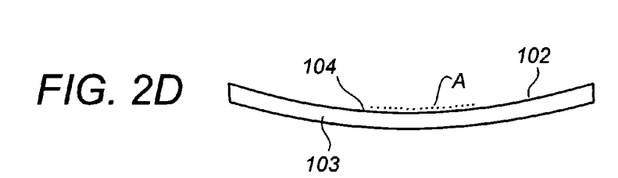
Figure 2E:
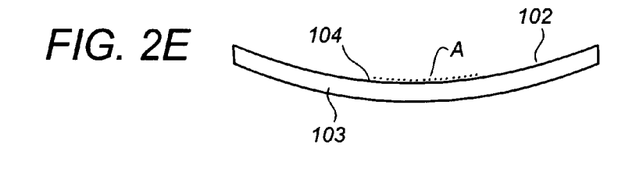

FIG. 1 illustrates a surface-enhanced Raman spectroscopy (SERS) system 100 including an apparatus for facilitating SERS according to an embodiment. SERS system 100 comprises a SERS-active structure 102 upon which analyte molecules "A" are disposed, a radiation source 106, and a detector 108. The radiation source 106 provides a strong monochromatic light beam "S," a monochromatic spectrum 114 thereof being illustrated in FIG. 1 as a plot of intensity versus wavenumber. The light beam "S" typically has a spot size of about 1 µm-5 µm. An exemplary range of wavelengths that may be emitted by the radiation source 106 includes wavelengths between about 350 nm and about 1000 nm.

Radiation "R" that emerges from the analyte molecules "A" and SERS-active structure 102 comprises a reflected and/or Rayleigh component 116 and a Raman component 118. The detector 108 optically filters out the reflected and/or Rayleigh component 116 and detects an intensity of the Raman scattered radiation 118 for each wavelength near the incident wavelength. Typically, a processor 110 controls the radiation source 106 and the detector 108, and receives readings from the detector to produce a Raman spectrum readout, the peaks and valleys of which are then used for analyzing the analyte molecules "A." The Raman spectrum readout is often presented as a plot of intensity versus Raman shift, the Raman shift being defined as the difference $v_R$ between the wavenumbers of the source and Raman-scattered radiation. Peaks and valleys that are meaningful for purposes of chemical analysis are often for Raman shifts in the range of 500 cm$^{-1}$-2000 cm$^{-1}$, which for a typical source wavelength of 1000 nm would correspond to Raman-scattered photons having wavelengths between 1050 nm-1250 nm.

SERS-active structure 102 comprises a substrate 103 having a patterned arrangement 104 of SERS-active material nanosections 105 thereon. To illustrate the wide variety of patterned arrangements of SERS-active material nanosections that are within the scope of the present teachings, FIG. 1 illustrates two arrangements 104 and 104'. In arrangement 104, each nanosection 105 is a separate particle of SERS-active material. In an alternative arrangement 104', the substrate 103 is coated with a single roughened metallic layer, with adjacent portions thereof constituting each SERS-active material nanoparticle 105'. In the context of the nanoparticles 105/105', it is to be noted that the terms pattern and arrangement herein are generally used with reference to all three spatial dimensions, and are only used in the sense of two-dimensional "aerial" patterns/arrangements in cases where the nanostructures are very thin and flat. Examples of suitable SERS-active materials include gold, silver, copper, platinum, palladium, titanium, and aluminum, and other materials exhibiting analogous SERS-active characteristics.

The SERS-active structure 102 is preferably derivatized or functionalized by attachment of receptors or ligands (not shown) that promote the binding of a particular analyte molecule in close proximity to the SERS-active material nanosections 105. The ligand may be repulsive or neutral relative to other molecules. The ligand and the analyte molecule may consist of what is often referred to as a specific pair or a recognition pair of molecules. The particular analyte molecule may include, but is not limited to, biomolecules such as nucleic acids, proteins, hormones, sugars, and metabolites. The ligand may include, but is not limited to, antibodies, receptors, and nucleic acids. Techniques for functionalizing surfaces for attachment of particular analyte molecules thereto have been researched and developed extensively in the art of biosensors and bioassays and can be employed.

Typically, the Raman scattered photons are scattered isotropically from the analyte molecules. Thus, the position of the detector 108 relative to the source 106 and SERS-active structure 102 does not substantially affect the intensity of Raman signal received. Nevertheless, for one embodiment, the detector 108 may be positioned at, for example, an angle of 90 degrees relative to the source direction to minimize the intensity of the reflected and/or Rayleigh-scattered radiation incident thereon.

According to an embodiment, also provided is an actuator 112 in actuable communication with the SERS-active structure 102 to deform the SERS-active structure 102 while the analyte molecules "A" are disposed therenear. It has been found that, due to the high sensitivity of hot-spot formation and extinction to even small variations in local arrangements of SERS-active material nanostructures, a substantial degree of control can be achieved over that amount of Raman intensification provided.

Figure 3:
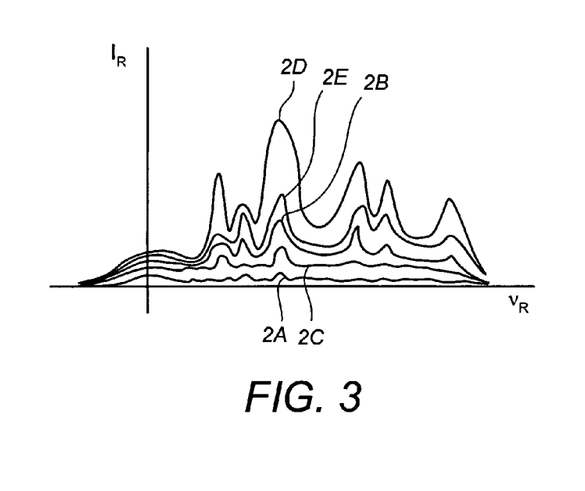
FIG. 3 illustrates conceptual examples of Raman spectra associated with the SERS-active structure of FIGS. 2A-2E.

FIGS. 2A-2E illustrate the SERS-active structure 102 at different amounts of deformation according to an embodiment, while FIG. 3 illustrates conceptual examples of the Raman spectra associated with the SERS-active structure 102. Advantageously, in accordance with an embodiment, the amount of intensification provided by the SERS-active structure 102 can be tuned by controlling the amount of deformation thereof, and this tuning can be performed in real-time as actual analyte molecules are being sensed.

In the example of FIGS. 2A-2E, the SERS-active structure 102 undergoes out-of-plane concave and convex deformations. However, it is to be appreciated that many types of out-of-plane bows, bends, twists, and contour changes are within the scope of the present teachings. It is also to be appreciated that the "natural," non-actuated shape of the SERS-active structure 102 can itself be non-planar, wherein the out-of-plane deformations induce transformation from a first non-planar shape to a second non-planar shape.

The substrate 103 should comprise a material having sufficient flexibility to achieve the deformations shown and described, and its selection will depend heavily on the amount of deformation desired. For very large desired deformations tending toward ellipsoidal or spherical shapes, a stretchable and resilient polymer membrane can be used. On the other hand, in other embodiments such as those described infra with respect to FIGS. 4-5, the amount of deformation required is very modest, such as on the order of 1 percent or less. For those embodiments, substrate 103 can comprise more rigid materials such as one or more of silicon, a metal, a III-V semiconductor material, a glass, a hard polymer, and a II-VI semiconductor material, preferably processed to have a thickness less than a few microns, although the scope of the present teachings is not so limited.

Figure 4:
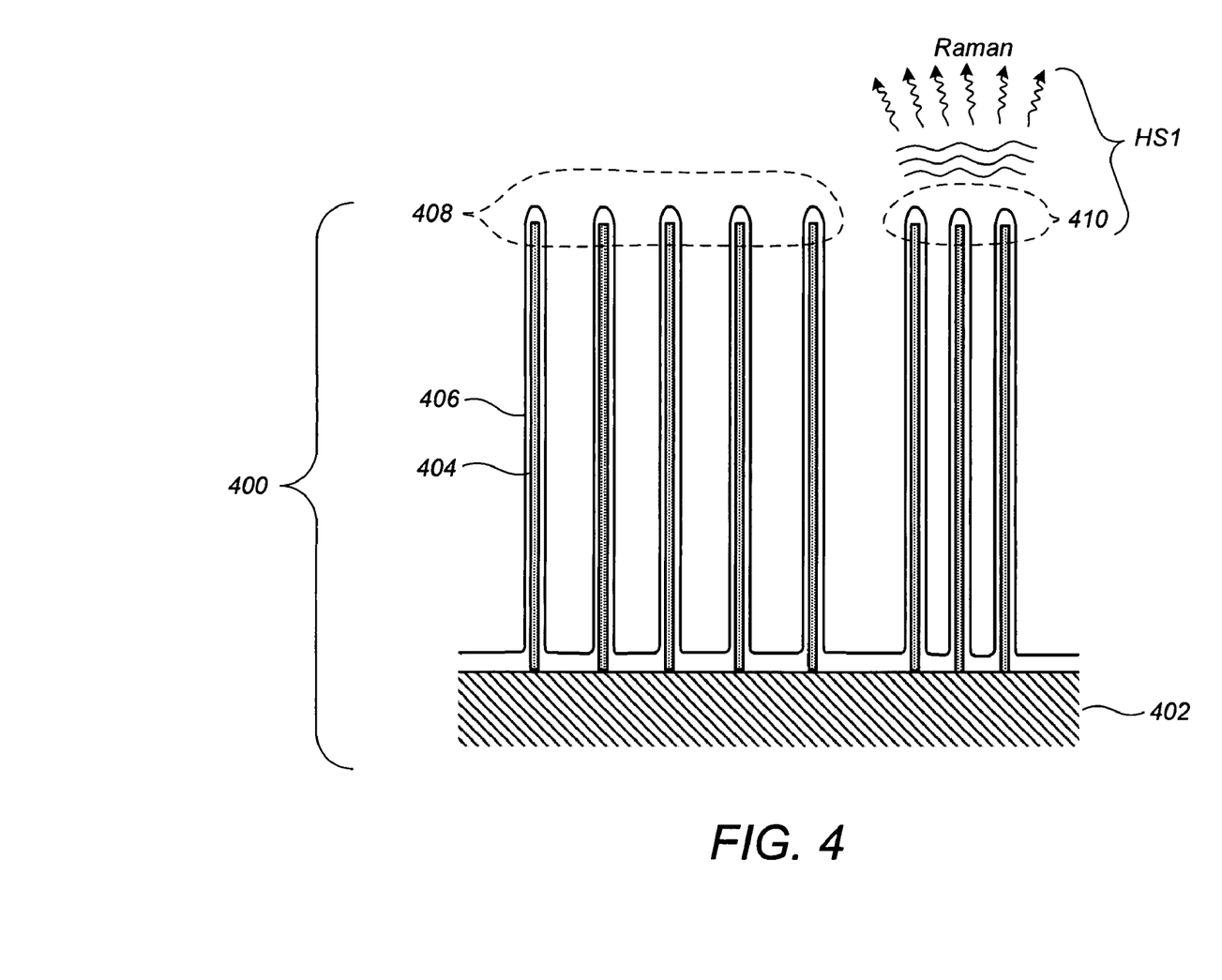
FIG. 4 illustrates a side cut-away view of a SERS-active structure according to an embodiment.
Figure 5:
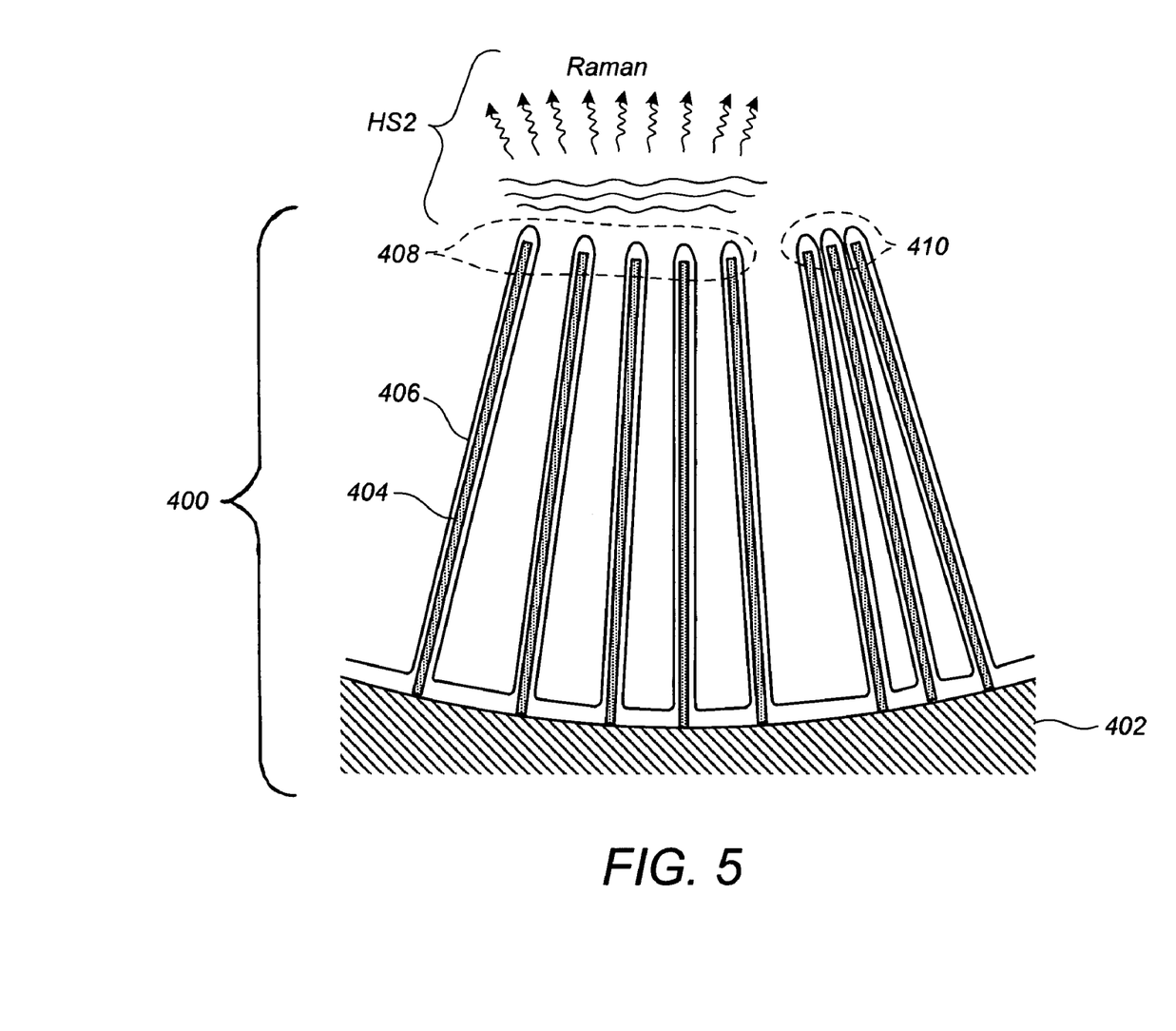
FIG. 5 illustrates a side cut-away view of the SERS-active structure under an amount of concave deformation.

FIG. 4 illustrates a conceptual side cut-away view of a SERS-active structure 400 according to an embodiment. FIG. 5 illustrates a conceptual side cut-away view of the SERS-active structure 400 under an amount of deformation. SERS-active structure 400 comprises a plurality (generally a large population) of high aspect-ratio nanowires 404 formed on a substrate 402. The nanowires 404 and substrate 402 can comprise, for example, silicon, a III-V semiconductor material or a II-VI semiconductor material, and the nanowires 404 can be formed on the substrate 402 using known methods. The diameters of the nanowires 404 can be in the range of 5 nm to 200 nm, although the other sizes are not outside the scope of the present teachings. SERS-active structure 400 further comprises an arrangement of nanosections of SERS-active material 406 including a first grouping 408 and a second grouping 410 thereof. Although shown as conformally deposited on the entire length of the nanowires 404 and atop the substrate 402 in FIG. 4, in other embodiments the SERS-active material can be formed just at the tips of the nanowires 404 using any of a variety of methods, and resulting in any of a variety of well-defined, blob-like, random, and/or pseudorandom shapes.

According to an embodiment, the nanowires 404 have a very high aspect ratio, preferably 50:1 or greater, such that relatively small deformations of the substrate 402 can result in very substantial changes in the patterns of SERS-material nanosections present near the tips of the nanowires. Accordingly, deformations on the order of 1 percent or less can result in very substantial changes in the patterns, sufficient to substantially alter localized hot-spot conditions across the SERS-active structure 400. By way of illustration, in FIG. 4 the second group 410 of SERS-material nanosections is just right for producing a hot-spot HS1, thereby causing a large increase in inelastic scattering by a nearby analyte molecule (not shown). In contrast, the first group 408 does not form a hot spot. However, after a small amount of deformation as shown in FIG. 5 (the amount is exaggerated for purposes of this example), there has been a shift in the patterns of SERS-material nanosections, and now it is the first group 408 that forms a hot spot HS2, while the hot spot HS1 is extinguished.

It is to be appreciated that the example of FIGS. 4-5 is highly simplified and conceptualized for clarity of description. For example, although the nanowires 404 are shown as extending in a precisely vertical manner in FIG. 4, in practical implementations the nanowires 404 may outwardly extend from the surface at any of a variety of different angles, both in an absolute sense relative to the surface and in a relative sense compared to each other. Moreover, in practical implementations the nanowires 404 will often have a degree of branching in which, as known in the art, there are multiple tips for a single nanowire stem. Using known methods, the fabrication of the nanowires 404 can be modified as needed to absolutely and/or statistically regulate the outward projection angles of the nanowires and/or their branching characteristics to achieve the devices described herein.

Advantageously, the high aspect ratios of the nanowires 404 provides an ability for drastic pattern changes at their tips, including topology-amplifying, topology-reducing, and topology-destroying pattern changes. In accordance with an embodiment, a rich variety of hot spot creation and extinction scenarios can be provided by strategic selection—including ordered, random, pseudorandom, chirped, etc.—of different lengths, aspect ratios, and spacings, and patterns for the nanowires 404, whereby deformable actuation of the SERS-active structure 400 even by small amounts achieves substantial control over the amount of Raman intensification provided. For another embodiment, one or more of the nanowires 404 can include one or more branches, the number and placement of which can be at least partially controlled using known methods, and nanosections of SERS-active material can be formed upon the branch ends or otherwise or incorporated into the branch structure. In this manner, an even richer range of possibilities for hot-spot creation, sizing, and extinction can be provided.

Thus, according to an embodiment, a SERS-active structure is provided comprising a plurality of nanosections of SERS-active material geometrically arranged upon a plurality of nanostructures, wherein the nanostructures are configured and dimensioned such that relatively small variations in the surface concavity and surface convexity, or other out-of-plane shape variations, perturb the geometric arrangement of the nanosections of SERS-active material by an amount sufficient to substantially vary the hot-spot conditions across the SERS-active structure. Therefore, provided is the ability to modulate, control, and/or tune the intensity of radiation Raman-scattered from the analyte molecule by controlling the amount of SERS-induced Raman signal intensification.

Figure 6:
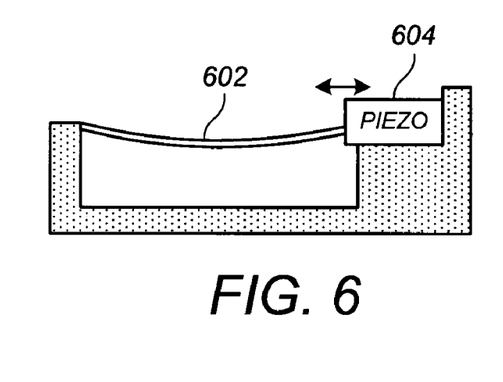
FIG. 6 illustrates an apparatus for facilitating SERS according to an embodiment having mechanically actuated deformation of a SERS-active structure.

FIGS. 6-9 illustrate some examples of different actuation configurations that can be used in accordance with one or more of the embodiments, although it is to be appreciated that many other configurations based on a variety of different actuation methodologies may be used without departing from the scope of the present teachings. The actuation configurations of FIGS. 6-9 can be used as alternatives to the actuation configuration shown in FIG. 1, supra, to achieve the controlled deformation of SERS-active structures according to the embodiments. FIG. 6 illustrates a SERS facilitation apparatus according to an embodiment in which a concavity (or a convexity) of a SERS-active structure 602 having a generally rigid substrate is controlled by a piezoelectric actuator 604 that moves in an in-plane direction. Advantageously, because only a modest amount of deformation is usually required (e.g., on the order of 1 percent or less), the substrate can comprise a variety different solid materials, even many crystalline materials, without incurring breakage in the deformation process.

Figure 7:
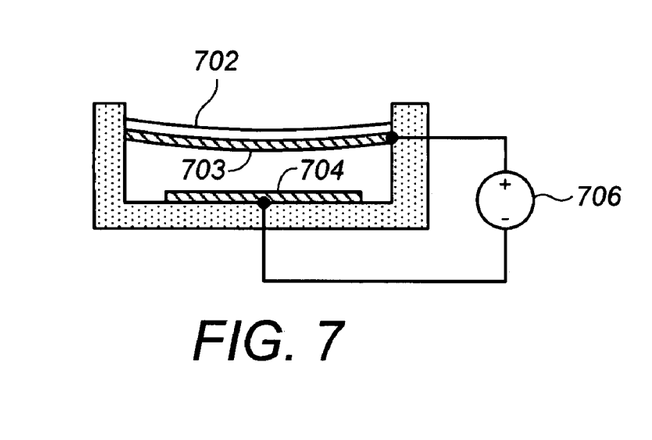
FIG. 7 illustrates an apparatus for facilitating SERS according to an embodiment having electrostatically actuated deformation of a SERS-active structure.

FIG. 7 illustrates a SERS facilitation apparatus according to an embodiment for which a concavity (or a convexity) of a SERS-active structure 702 is electrostatically actuated. A metal layer 703 is attached to a substrate of the SERS-active structure 702, a metal plate 704 is attached to a nearby fixed surface, and a voltage is applied between the metal layer 703 and the metal plate 704, the SERS-active structure 702 deforming by electrostatic forces between the plates. Any of a variety of other types of microelectromechanical (MEMS) actuation schemes are also within the scope of the present teachings.

Figure 8:
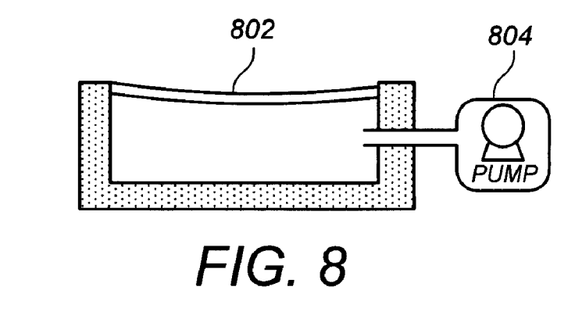
FIG. 8 illustrates an apparatus for facilitating SERS according to an embodiment having pneumatically actuated deformation of a SERS-active structure.

FIG. 8 illustrates a SERS facilitation apparatus according to an embodiment for which a concavity (or a convexity) of a SERS-active structure 802 is pneumatically actuated by a fluid pump 804. The use of pneumatic actuation can be less advantageous than mechanical or electromagnetic actuation in circumstances where high rates of variation in the deformation of the SERS-active structure are desired. Also, because of the generally uniform forces incurred across the affected surface, pneumatic actuation can be less advantageous than mechanical or electromagnetic actuation in circumstances where localized or spatially variable deformation forces are desired.

Figure 9:
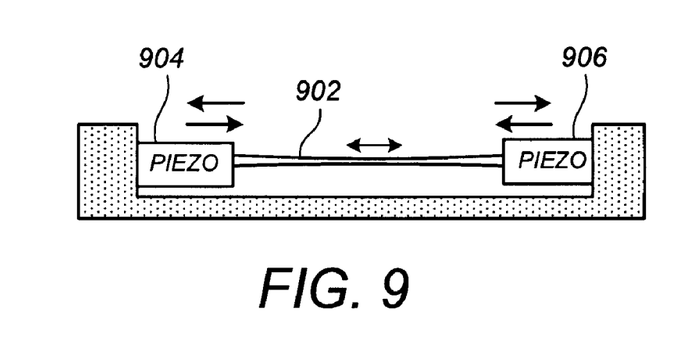
FIG. 9 illustrates an apparatus for facilitating SERS according to an embodiment having mechanically actuated in-plane expansion and/or contraction of a SERS-active structure.

FIG. 9 illustrates a SERS facilitation apparatus according to an embodiment in which a SERS-active structure 902 comprises a stretchable polymeric membrane upon which is disposed spatial arrangements of nanosections of SERS-active material. The spatial arrangement of the nanosections of SERS-active material is varied in accordance with a stretching and/or relaxation of the polymeric membrane by piezoelectric actuators 904 and 906, thereby providing at least some variation in the amount of Raman intensification provided by the SERS-active structure 902.

Generally speaking, in-plane expansion and contraction of the substrate in FIG. 9 results in relatively affine variations in the patterns of SERS-active nanosections thereon. For a given amount of actuation effort, embodiments using such in-plane expansion and contraction of the substrate can result in a lesser amount of achievable control of the Raman intensification when compared to the previously-described combination of concave or convex deformations of the substrate with high aspect ratio nanostructures supporting (or being part of) SERS-active nanosections thereon. Similar comments apply for the case of concave or convex deformations of the substrate when mostly flat or low aspect ratio nanostructures are present, that is, the pattern variations in the SERS-active nanosections will tend to be affine and less pronounced, which can result in a lesser amount of achievable control of the Raman intensification when compared to the previously-described combination of concave or convex deformations of the substrate with high aspect ratio nanostructures supporting (or being part of) SERS-active nanosections thereon.

Whereas many alterations and modifications of the embodiments will no doubt become apparent to a person of ordinary skill in the art after having read the foregoing description, it is to be understood that the particular embodiments shown and described by way of illustration are in no way intended to be considered limiting. By way of example, although the controlled deformations are preferably applied dynamically in a real-time field environment to improve field results, in other embodiments the actuated deformation of a SERS-active substrate can be used during device fabrication and/or calibration to improve overall device quality. By way of further example, the present teachings can be used with hyper Raman spectroscopy in which higher order harmonics of the source radiation are considered.

By way of still further example, multiple similar or different deformable SERS-active substrates can be arrayed together and jointly or separately actuated for use in conjunction with a single laser source or multiple laser sources to achieve any of a variety of goals including, but not limited to, portability, dependability, reusability, cost efficiency, calibration reliability, and/or adaptability for differing analyte molecule types, without departing from the scope of the present teachings. Alternatively, a single deformable SERS-active substrate can be actuated in different areas by multiple different actuators to achieve such goals without departing from the scope of the present teachings. Optionally, single-chip or multi-chip arrays of deformable SERS-active substrates may be incorporated within, or otherwise in conjunction with, other MEMS-actuated SERS system components, such as the wavelength-tunable Fabry-Perot radiation amplifying structures described in the commonly assigned US 2006/0055920A1. By way of even further example, multiple similar or different deformable SERS-active substrates can be arrayed together and jointly or separately actuated for use in conjunction with a single laser source or multiple laser sources to achieve any of a variety of goals including, but not limited to, portability, dependability, reusability, cost efficiency, calibration reliability, and/or adaptability for differing analyte molecule types, without departing from the scope of the present teachings.

Alternatively, a single deformable SERS-active substrate can be actuated in different areas by multiple different actuators to achieve such goals without departing from the scope of the present teachings. Trench-based schemes for SERS-active structures analogous to the above-described nanowire-based schemes are also within the scope of the present teachings. Thus, reference to the details of the described embodiments are not intended to limit their scope.

What is claimed is:

1. An apparatus for facilitating surface-enhanced Raman spectroscopy (SERS), comprising:
   a SERS-active structure near which a plurality of analyte molecules are disposed; and
   an actuation device in actuable communication with the SERS-active structure to deform the SERS-active structure while said analyte molecules are disposed therenear, said deformation of the SERS-active structure varying an intensity of radiation Raman-scattered from the analyte molecules, wherein said actuation device deforms the SERS-active structure by varying at least one of a surface concavity and surface convexity thereof in a vicinity of the analyte molecules, and said SERS-active structure comprising a plurality of nanosections of SERS-active material geometrically arranged upon a plurality of nanostructures, wherein said nanostructures are configured and dimensioned such that relatively small variations in said at least one of the surface concavity and surface convexity perturb said geometric arrangement of said nanosections of SERS-active material by an amount sufficient to vary a plurality of hot-spot conditions across said SERS-active structure and thereby vary said intensity of radiation Raman-scattered from the analyte molecules.

2. An apparatus for facilitating surface-enhanced Raman spectroscopy (SERS), comprising:
   a SERS-active structure near which a plurality of analyte molecules are disposed; and
   an actuation device in actuable communication with the SERS-active structure to deform the SERS-active structure while said analyte molecules are disposed therenear, said deformation of the SERS-active structure varying an intensity of radiation Raman scattered from the analyte molecules, wherein said actuation device deforms the SERS-active structure by varying at least one of a surface concavity and surface convexity thereof in a vicinity of the analyte molecules, and wherein said SERS-active structure comprises:

a substrate;

a plurality of nanostructures outwardly extending from said substrate; and a plurality of nanosections of SERS-active material formed on said nanostructures;

wherein by said nanostructures outwardly extend from said substrate by an amount sufficient such that relatively small variations in said at least one of the surface concavity and surface convexity perturb a relative geometric arrangement of said nanosections of SERS-active material by an amount sufficient to vary said intensity of radiation Raman-scattered from the analyte molecules.

3. The apparatus of claim 2, wherein said nanostructures are nanowires having an average aspect ratio of at least 50:1.

4. The apparatus of claim 3, wherein said nanowires are random, pseudorandom, or chirped with respect to at least one of size, aspect ratio, position, outward projection angle, number of branches thereon, and placement of branches thereon.

5. The apparatus of claim 2, wherein said substrate comprises one of silicon, a metal, a Ill-V semiconductor material, a II-VI semiconductor material, and a polymer, and wherein said SERS-active material comprises one of gold, silver, copper, platinum, palladium, titanium, and aluminum.

6. A method for facilitating surface-enhanced Raman spectroscopy (SERS), comprising:

receiving a plurality of analyte molecules for attachment near a SERS-active structure; and deforming the SERS-active structure in a vicinity of the received analyte molecules to vary an intensity of radiation Raman-scattered therefrom, wherein said deforming comprises varying at least one of a surface concavity and surface convexity of the SERS-active structure, and wherein said deforming comprises introducing relatively small variations in said at least one of the surface concavity and surface convexity of the SERS-active structure, said SERS-active structure comprising a plurality of nanosections of SERS-active material geometrically arranged upon a plurality of nanostructures, said relatively small variations perturbing said geometric arrangement of said nanosections by an amount sufficient to vary a plurality of hot-spot conditions across said SERS-active structure to thereby vary the intensity of radiation Raman-scattered from the analyte molecules.

7. A method for facilitating surface-enhanced Raman spectroscopy (SERS), comprising:

receiving a plurality of analyte molecules for attachment near a SERS-active structure; and deforming the SERS-active structure in a vicinity of the received analyte molecules to vary an intensity of radiation Raman-scattered therefrom, wherein said deforming comprises varying at least one of a surface concavity and surface convexity of the SERS-active structure, and wherein said deforming comprises introducing relatively small variations in said at least one of the surface concavity and surface convexity of the SERS-active structure, said SERS-active structure comprising a substrate, a plurality of nanostructures outwardly extending from said substrate, and a plurality of nanosections of SERS-active material formed on said nanostructures, said nanostructures outwardly extending from said substrate by an amount sufficient such that said relatively small variations perturb a relative geometric arrangement of said nanosections by an amount sufficient to vary the intensity of radiation Raman-scattered from the analyte molecules.

8. An apparatus for use in surface-enhanced Raman spectroscopy (SERS), comprising means for deforming a SERS-active structure upon which a plurality of analyte molecules are disposed to vary an intensity of radiation Raman-scattered from the analyte molecules, wherein said means for deforming comprises means for varying at least one of a surface concavity and surface convexity of the SERS-active structure, and said SERS-active structure comprises:

a plurality of nanosections of SERS-active material; and means for moveably supporting said plurality of nanosections such that relatively small variations in said at least one of the surface concavity and surface convexity perturb a geometric arrangement of said nanosections by an amount sufficient to vary a plurality of hot-spot conditions across said SERS-active structure and thereby vary the intensity of radiation Raman-scattered from the analyte molecules.

9. The apparatus of claim 8, wherein means for moveably supporting comprises:

a substrate; and a plurality of nanostructures upon which said nanosections of SERS-active material are formed, said plurality of nanostructures outwardly extending from said substrate;

wherein said nanostructures outwardly extend from said substrate by an amount sufficient such that said relatively small variations in said at least one of the surface concavity and surface convexity provide for said sufficient perturbation of said geometric arrangement of said nano sections.

10. The apparatus of claim 9, wherein said nano structures are nanowires having an average aspect ratio of at least 50:1.

11. The apparatus of claim 10, wherein said nanowires are random or pseudorandom with respect to at least one of size, aspect ratio, position, outward projection angle, number of branches thereon, and placement of branches thereon.

12. The apparatus of claim 1, wherein said nanostructures are nanowires having an average aspect ratio of at least 50:1.

13. The apparatus of claim 12, wherein said nanowires are random, pseudorandom, or chirped with respect to at least one of size, aspect ratio, position, outward projection angle, number of branches thereon, and placement of branches thereon.

14. The apparatus of claim 1, wherein said substrate comprises one of silicon, a metal, a III-V semiconductor material, a II-VI semiconductor material, and a polymer, and wherein said SERS-active material comprises one of gold, silver, copper, platinum, palladium, titanium, and aluminum.

15. The apparatus of claim 1, wherein said SERS-active structure further comprises a stretchable polymeric membrane upon which said nanosections of SERS-active material are geometrically arranged upon said plurality of nanostructures.

16. The apparatus of claim 2, wherein said substrate further comprises a stretchable polymeric membrane upon which said nanosections of SERS-active material are geometrically arranged upon said plurality of nanostructures.

17. The apparatus of claim 6, wherein said deforming comprises controlling an actuation device that deforms said SERS-active structure, said actuation device comprising a pneumatically actuated fluid pump.

18. The apparatus of claim 17, wherein said SERS-active structure further comprises a stretchable polymeric membrane upon which said nanosections of SERS-active material are geometrically arranged upon said plurality of nanostructures, and said deforming comprise stretching said polymeric membrane.

19. The method of claim 7, wherein said deforming comprises controlling an actuation device that deforms said SERS-active structure, said actuation device comprising a pneumatically actuated fluid pump.

20. The method of claim 19, wherein said SERS-active structure further comprises a stretchable polymeric membrane upon which said nanosections of SERS-active material are geometrically arranged upon said plurality of nanostructures, and said deforming comprise stretching said polymeric membrane.

* * * * *

UNITED STATES PATENT AND TRADEMARK OFFICE
CERTIFICATE OF CORRECTION

PATENT NO. : 7,528,948 B2
APPLICATION NO. : 11/493477
DATED : May 5, 2009
INVENTOR(S) : Alexandre Bratkovski et al.

It is certified that error appears in the above-identified patent and that said Letters Patent is hereby corrected as shown below:

In column 9, line 3, in Claim 2, delete "Raman scattered" and insert -- Raman-scattered --, therefor.

In column 9, line 29, in Claim 5, delete "Ill" and insert -- III --, therefor.

In column 10, line 37, in Claim 9, delete "nano sections." and insert -- nanosections. --, therefor.

In column 10, line 38, in Claim 10, delete "nano structures" and insert -- nanostructures --, therefor.

Signed and Sealed this

Sixth Day of April, 2010

David J. Kappos
*Director of the United States Patent and Trademark Office*